United States Patent [19]

Commons et al.

[11] Patent Number: 4,812,583
[45] Date of Patent: Mar. 14, 1989

[54] SUBSTITUTED ACYLOXYALKYLPHENYLETHYLENE INHIBITORS OF 3-HYDROXY-3-METHYLGLUTARYL-COA REDUCTASE

[75] Inventors: Thomas J. Commons, Wayne; Richard E. Mewshaw, King of Prussia; Donald P. Strike, St. Davids, all of Pa.

[73] Assignee: American Home Products Corporation, New York, N.Y.

[21] Appl. No.: 95,800

[22] Filed: Sep. 11, 1987

[51] Int. Cl.[4] .......................................... C07D 309/30
[52] U.S. Cl. .................................................. 549/292
[58] Field of Search ......................... 549/292; 514/460

[56] References Cited

U.S. PATENT DOCUMENTS

| 4,375,475 | 3/1983 | Willard et al. | 549/292 |
| 4,571,428 | 2/1986 | Kapa | 556/437 |
| 4,613,610 | 9/1986 | Wareing | 514/406 |
| 4,654,363 | 3/1987 | Prugh | 549/292 |
| 4,661,483 | 4/1987 | Hoffman et al. | 514/316 |

FOREIGN PATENT DOCUMENTS

| 8500653 | 6/1986 | European Pat. Off. |  |
| 2162179 | 1/1986 | United Kingdom | 549/292 |

OTHER PUBLICATIONS

Derwent 84-201398/32 (Abstract of WO 8402-903).
Hoffman et al., J. Med. Chem. 29, 159 (1986).
Rosen et al., J. Am. Chem. Soc. 107, 3731 (1985).
Sato et al., Chem. Pharm. Bull. 28(5), 1509-1525 (1980).
Sletzinger et al., Tetrahedron Letters 26, 2951 (1985).
Stokker et al., J. Med. Chem. 28, 347 (1985).
Stokker et al., J. Med. Chem. 29, 170 (1986).

*Primary Examiner*—Richard L. Raymond
*Assistant Examiner*—Patricia L. Morris
*Attorney, Agent, or Firm*—Richard K. Jackson

[57] ABSTRACT

Compounds of the formula:

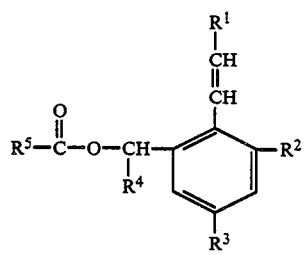

in which

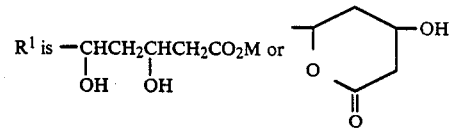

where M is hydrogen or alkyl; $R^2$ and $R^3$ are, independently, alkyl; $R^4$ is hydrogen, alkyl, phenyl or substituted phenyl, trifluoromethyl; and $R^5$ is alkyl, phenyl or substituted phenyl, alkoxy, or trifluoromethyl; or a pharmaceutically acceptable salt thereof, are hypocholesteremic agents.

6 Claims, No Drawings

SUBSTITUTED ACYLOXYALKYLPHENYLETHYLENE INHIBITORS OF 3-HYDROXY-3-METHYLGLUTARYL-COA REDUCTASE

BACKGROUND OF THE INVENTION

With the discovery that biosynthesis of cholesterol could be inhibited by compactin, and more effectively by mevinolin, considerable effort has been made in the attempt to obtain 3-hydroxy-3-methylglutaryl-coenzyme A reductase (HMG-CoA reductase) inhibitors of less complex structure, with limited success.

DESCRIPTION OF THE INVENTION

In accordance with this invention, there is provided a group of acyloxyalkylphenylethylene derivatives which possess HMG-CoA reductase inhibitors properties useful as antihypercholestermic agents in the treatment of disease states such as atherosclerosis, familial hypercholesterolaemia, hyperlipaemia, and the like. The acyloxyalkylphenylethylene derivatives of this invention possess the following structural features:

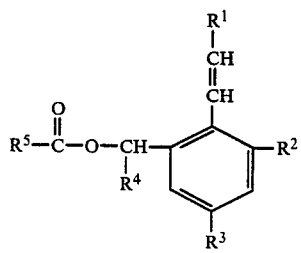

in which

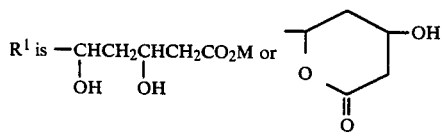

where

M is hydrogen or alkyl of 1 to 4 carbon atoms;

$R^2$ and $R^3$ are, independently, alkyl of 1 to 6 carbon atoms;

$R^4$ is hydrogen, alkyl of 1 to 10 carbon atoms, trifluoromehyl, phenyl or substituted phenyl, where the substituent is alkyl of 1 to 8 carbon atoms, alkoxy of 1 to 8 carbon atoms, or trifluoromethyl; and $R^5$ is alkyl of 1 to 10 carbon atoms, phenyl or substituted phenyl where the substituent is alkyl of 1 to 8 carbon atoms, alkoxy of 1 to 8 carbon atoms, or trifluoromethyl;

or a pharmaceutically acceptable salt thereof.

The preferred compounds of this invention from the standpoint of production economics and availability of starting materials, are those of the formula:

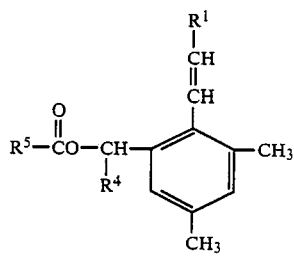

in which

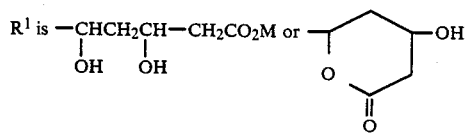

where

M is hydrogen or alkyl of 1 to 4 carbon atoms;

$R^4$ is hydrogen, alkyl of 1 to 10 carbon atoms or phenyl; and $R^5$ is alkyl of 1 to 6 carbon atoms;

or a pharmaceutically acceptable salt thereof.

In the above-described group of compounds, the alkyl and alkoxy groups may be straight or branched chain and the pharmaceutically acceptable salts are those derived conventionally from inorganic or organic bases which will neutralize the carboxylic acid where M is hydrogen, to supply the alkali metal (sodium or potassium), alkaline earth metal (calcium or magnesium), ammonium or amine (methylamine, ethylamine, propylamine, isopropylamine, dimethylamine, diethylamine, di(hydroxyethyl)amine, and the like) cations.

The lactone (4-hydroxy-2H-pyran-2-one) group may be hydrolyzed or enzymatically opened in situ to afford the dihydroxypentanoic acid group as a functional species which is usually the more potent form of the compound, at least in in vitro studies. The trans configuration of the tetrahydro-4-hydroxy-2H-pyran-2-one ring is preferred to the cis configuration. The configuration of the trans-tetrahydropyran moiety of the compounds exemplified infra is composed of the 4R, 6S isomer and the racemate (i.e. 4S,6R). Positions 4 and 6 of the pyranone ring and 3 to 5 positions of the dihydroxypentanoic acid form of the compounds and the acyloxy bearing methyl group present chiral centers. The optical isomers are separated conventionally. Hence, throughout this specification and the appended claims, reference to the compounds is intended to embrace their stereo and optical isomers as well as racemic mixtures.

The compounds of this invention may be prepared by a variety of synthetic routes using conventional methods beginning with an appropriately substituted 2-bromocinnamic acid derivative [Stokker et al., J. Med. Chem., 29, 170, Scheme IV (1986), see Scheme IV on page 172]. The technique employed here involves conversion of the carboxyl group to an aldehyde and protection of the aldehyde as an acetal during metalation at the 2-position followed by reaction with the appropriate aldehyde $R^4$CHO to obtain the

group. Where $R^4$ is hydrogen, formylation of the metalated acetal provides the desired formyl substitution which upon reduction yields the corresponding alcohol

The alcohol is acylated with the desired acid halide $R^5COX$ (X=Cl or Br) in THF with n-butyllithium or more preferably in methylene chloride with 4-dimethylaminopyridine (DMAP). Subsequent hydrolysis of the acetal yields the substituted cinnamaldehyde which is reacted with the dianion of acetoacetic acid methyl ester. Selective reduction of the keto group provides the dihydroxy heptenoic acid ester. Conversion to the heptenoic acid and dehydration provides the 5-hydroxy lactone final product which is converted to a pharmaceutically acceptable heptenoic acid salt by reaction with an equivalent of the desired base.

The following examples illustrate the method employed to produce representative compounds of this invention. Example 1 provides complete details in the preparation of each intermediate involved. The other examples follow the procedure of Example 1 unless otherwise noted.

EXAMPLE 1

2,2-Dimethylbutanoic acid[4α,6β(E)]-1-[2-[2-tetrahydro-4-hydroxy-6-oxo-2H-pyran-2-yl)ethenyl]-3,5-dimethylphenyl]butyl ester A solution of 5.07 g (19.9 mmol) of 3-(2-bromo-4,6-dimethylphenyl)-2-propenoic acid in 50 mL of thionyl chloride containing 50 µl of dimethylformamide (DMF) was stirred under nitrogen at room temperature for 20 hours. The volatiles were removed under reduced pressure to give 5.40 g (99%) of (E)-3-(2-bromo-4,6-dimethylphenyl)-2-propenoyl chloride as a dark brown solid: IR (film) 2960, 2920, 1750, 1620 and 1605 cm$^{-1}$; NMR (CDCl$_3$) δ 2.32 (3H, s), 2.40 (3H, s), 6.44 (1H, d, J=16 Hz).

Bis(triphenylphosphine) copper (I) borohydride (8.82 g, 146 mmol) was added in portions over 5 minutes to a solution of (E)-3-(2-bromo-4,6-dimethylphenyl)-2-propenoyl chloride (4.00 g, 146 mmol) and triphenylphosphine (7.66 g, 292 mmol) in 200 mL of acetone under a nitrogen atmosphere. After the addition was complete the mixture was stirred at room temperature for 3.5 hours. The solid formed was removed by filtration and the filtrate concentrated under reduced pressure to give a solid. Trituration of this material with diethyl ether and removal of the ether under reduced pressure gave 6.00 g of a light brown solid. Purification by high pressure liquid chromatography (HPLC) gave (E)-3-(2-bromo-4,6-dimethylphenyl)-2-propenal as a white crystalline solid: mp 99°-103° C.; IR (KBr) 2910, 2820, 1655, 1615 and 1600 cm$^{-1}$; NMR (DMSO-d$_6$) δ 2.30 (3H, s), 2.36 (3H, s), 6.50 (1H, dd, J=9, 15 Hz), 7.18 (1H, s), 7.46 (1H, s), 7.80 (1H, d, J=15 Hz), 9.77 (1H, d, J=9 Hz).

Elemental Analysis for: C$_{11}$H$_{11}$BrO Calculated: C, 55.26; H, 4.63; Br, 32.42. Found: C, 54.99; H, 4.56; Br, 31.86.

A mixture of 1.00 g (4.19 mmol) of (E)-3-(2-bromo-4,6-dimethylphenyl)-2-propenal, 1.32 g (12.6 mmol) of 2,2-dimethyl-1,3-propanediol and a catalytic amount (65 mg) of p-toluenesulfonic acid monohydrate in 100 mL of dry benzene was heated at reflux in a Dean-Stark apparatus for 2 hours. The solution was washed with 1N sodium hydroxide, water (3 times), and the solvent removed under reduced pressure to give 1.32 g (97%) of (E)-2-[2-(2-bromo-4,6-dimethylphenyl)ethenyl]-5,5-dimethyl-1,3-dioxane as a white crystalline material. Purification by HPLC (70% CH$_2$Cl$_2$-Hexane) gave an analytically pure sample: mp 54°-56° C.; IR (KBr) 2960, 2860, 1670 and 1610 cm$^{-1}$; NMR (CDCl$_3$) δ 0.77 (3H, s), 1.25 (3H, s), 2.28 (3H, s), 2.37 (3H, s), 3.58 (2H, d, J=12 Hz), 3.74 (2H, d, J=12 Hz), 5.09 (1H, d, J=6 Hz), 5.90 (1H, dd, J=6, 15 Hz), 6.78 (1H, d, J=15 Hz), 6.96 (1H, s), 7.30 (1H, s).

Elemental Analysis for: C$_{16}$H$_{21}$BrO$_2$ Calculated: C, 59.09; H, 6.50; Br, 24.56. Found: C, 59.41; H, 6.71; Br, 25.10.

(E)-2-[2-(2-bromo-4,6-dimethylphenyl)ethenyl]-5,5-dimethyl-1,3-dioxane (1.50 g, 4.62 mmol) was dissolved in 75 mL of anhydrous THF, put under a N$_2$ atmosphere, and cooled to −78° C. To this solution was added dropwise a 1.3M solution of n-butyllithium in hexane (4.2 mL, 5.54 mmol). After the addition the solution was stirred at −78° C. for 30 minutes. n-Butyraldehyde (530 µl, 6.00 mmol) was then added, the cooling bath was removed and the stirring continued for 1 hour. The reaction was partitioned between ethyl acetate-water and extracted. The organic layer was washed two times with water, dried over anhydrous K$_2$CO$_3$ and the solvent removed under reduced pressure to give 1.73 g of an oil. Chromatography on silica gel (Merck 230-400 mesh) using 6:1 Hexane-EtOAc as an eluent gave (E)-2-[2-(5,5-dimethyl-1,3-dioxan-2-yl)ethenyl]3,5-dimethyl-α-propylbenzenemethanol (1.11 g, 75%) as a waxy solid: mp 56°-59° C.; IR (KBr) 3340, 2950, 2845, 1665 and 1610 cm$^{-1}$; NMR (DMSO-d$_6$) δ 0.72 (3H, s), 2.26 (3H, s), 3.52 (2H, d, J=10 Hz), 3.64 (2H, d, J=10 Hz), 4.68-4.76 (1H, m), 4.92 (1H, d, J=4 Hz, exchangeable), 5.06 (1H, d, J=6 Hz), 5.60 (1H, dd, J=6, 16 Hz), 6.72 (1H, d, J=16 Hz), 6.92 (1H, s), 7.16 (1H, s).

A 1.4M solution of n-butyllithium in hexane (2.6 mL, 3.61 mmol) was added dropwise under a nitrogen atmosphere to a solution of (E)-2-[2-(5,5-dimethyl-1,3-dioxan-2-yl)ethenyl]-3,5-dimethyl-α-propylbenzenemethanol (956.8 mg, 3.01 mmol) in 100 mL of dry THF. After the addition, the solution was stirred at room temperature for 15 minutes. 2,2-Dimethylbutyryl chloride (500 µl, 3.61 mmol) was then added and the solution stirred at room temperature for 30 minutes. The reaction was partitioned between 1N HCl-EtOAc and extracted. The organic layer was washed with water (two times), dried (anh. K$_2$CO$_3$) and the solvent removed under reduced pressure. Purification of the residual oil on 250 g of silica gel (Merck, 230-400 mesh) using 3:2 CH$_2$Cl$_2$-hexane as an eluent gave 2,2-dimethylbutanoic acid (E)-1-[2-[2-(5,5-dimethyl-1,3-dioxan-2-yl)ethenyl]-3,5-dimethylphenyl]butyl ester (534 mg, 43%) as an oil: IR (film) 2945, 2860, 1720 and 1605 cm$^{-1}$; NMR (DMSO-d$_6$) δ 0.68-0.80 (6H, m), 0.86 (3H, t, J=6 Hz), 1.07 (3H, s), 1.08 (3H, s), 1.12 (3H, s), 1.14-1.44 (2H, m), 1.46-1.66 (3H, m), 1.68-1.86 (1H, m), 1.18 (3H, s), 2.23 (3H, s), 3.54 (2H, d, J=10 Hz), 3.64 (2H, d, J=10 Hz), 5.09 (1H, d, J=5 Hz), 5.68 (1H, dd, J=5, 15 Hz), 5.74-5.86 (1H, m), 6.78 (1H, d, J=15 Hz), 6.98 (2H, s).

Elemental Analysis for: C$_{26}$H$_{40}$O$_4$ Calculated: C, 74.96; H, 9.68. Found: C, 75.08; H, 9.83.

A solution of 2,2-dimethylbutanoic acid (E)-1-[2-[2-(5,5-dimethyl-1,3-dioxan-2-yl)ethenyl]-3,5-dimethylphenyl]butyl ester (556 mg, 1.33 mmol) in 25 mL of acetone and 9 mL of water plus 100 μl of conc. $H_2SO_4$ was stirred at room temperature. The reaction was monitored by thin layer chromatography. At the end of the reaction the solution was partitioned between ethyl acetate-water and extracted. The organic layer was washed with water (five times), dried (anh. $MgSO_4$) and the solvent removed under reduced pressure to provide 411 mg of a oil. Purification of this oil on 150 g of silica gel (Merck, 230–400 mesh) using 6:1 hexane:ethyl acetate as an eluent gave 2,2-dimethylbutanoic acid (E)-1-[2-(formylethenyl)-3,5-dimethyl-phenyl]butyl ester as a crystalline material (398 mg, 90%): mp 32°–34° C.; IR (KBr) 2950, 2920, 2860, 1715, 1680 and 1605 cm$^{-1}$; NMR (CDCl$_3$) δ 0.76 (3H, t, J=9 Hz), 0.90 (3H, t, J=7 Hz), 1.14 (3H, s), 1.16 (3H, s), 1.20–1.50 (2H, m), 1.50–1.70 (3H, m), 1.80–1.96 (1H, m), 2.30 (3H, s), 2.32 (3H, s), 5.74–5.84 (1H, m), 6.36 (1H, dd, J=8, 15 Hz), 7.00 (1H, s), 7.08 (1H, s), 7.90 (1H, d, J=15 Hz), 9.78 (1H, d, J=8 Hz).

Elemental Analysis for: $C_{21}H_{30}O_3$ Calculated: C, 76.33; H, 9.15. Found: C, 76.54; H, 9.05.

Methyl acetoacetate (100 μl, 0.93 mmol) was added dropwise to a stirred suspension of sodium hydride (60% oil dispersion; 40.8 mg, 1.0 mmol) in 5 mL of anhydrous tetrahydrofuran at ice bath temperature under a nitrogen atmosphere. The resulting solution was stirred for 15 minutes at ice bath temperature and then treated with a 1.4M solution (728 μl, 1.0 mmol) of n-butyllithium in hexane over 5 minutes. The yellow solution was stirred at ice bath temperature for 15 minutes and then added dropwise over 10 minutes to a solution of the aldehyde prepared in the preceding paragraph in 5 mL of anhydrous tetrahydrofuran at ice bath temperature under a nitrogen atmosphere. The resulting solution was stirred for 15 minutes at ice bath temperature and then quenched by the dropwise addition of 12N HCl (167 μl, 2.0 mmoles). The mixture was diluted with water and extracted with ethyl acetate (three times). The organic extracts were washed with brine, dried over $MgSO_4$, and the solvent removed under reduced pressure to give 326 mg of a yellow oil. Purification of this oil on 150 g of silica gel (Merck, 230–400 mesh) using hexane-ethyl acetate (6:1 to 2:1) as an eluent gave (E)-7-[2-[1-(2,2-dimethyl-1-oxobutoxy)butyl]-4,6-dimethylphenyl]-5-hydroxy-2-oxo-6-heptenoic acid methyl ester as a clear oil (128 mg, 37%): IR (CHCl$_3$) 3500, 1740, 1710, 1655 and 1610 cm$^{-1}$; NMR (CDCl$_3$) δ 0.70–0.84 (3H, m), 0.90 (3H, t, J=6 Hz), 1.10–1.20 (6H, m), 1.20–1.50 (2H, m), 1.52–1.72 (3H, m), 1.72–1.90 (1H, m), 2.20 (6H, m), 1.20–1.50 (2H, m), 1.52–1.72 (3H, m), 1.72–1.90 (1H, m), 2.20 (3H, s), 2.28 (3H, s), 2.86–2.96 (2H, m), 3.58 (2H, s), 3.76 (3H, s), 4.78–4.88 (1H, m), 5.66–5.80 (1H, m), 5.92–6.00 (1H, m), 6.64–6.76 (1H, m), 6.94 (1H, s), 7.04 (1H, s).

Elemental Analysis for: $C_{26}H_{38}O_6$ Calculated: C, 69.93; H, 8.58. Found: C, 69.68; H, 8.56.

Triethylborane (360 μl of a 1M solution) was added to a solution of 107 mg (0.24 mmol) of the ketoester prepared in the preceding paragraph in 5 mL anhydrous tetrahydrofuran under a nitrogen atmosphere. Air (30 mL) was added and the solution stirred at room temperature for 15 minutes and then cooled to −78° C. Sodium borohydride (10.9 mg, 0.29 mmol) was added followed by the dropwise addition of molecular sieve dried MeOH. After the addition, the solution was stirred at −78° C. for 30 minutes. 30% Hydrogen peroxide (2 mL) in 5 mL of water was then added dropwise. After the addition, the cooling bath was removed and the stirring continued for 1 hour. The reaction was partitioned between 1N HCl-ethyl acetate and extracted. The organic layer was washed with water, dried over $MgSO_4$ and the solvent removed under reduced pressure to give 122 mg of an oil. Purification of the oil on silica gel (Merck, 230–400 mesh) using 2:1 hexane:ethyl acetate as an eluent gave 74 mg (68%) of (3R,5S,E)-7-[2-[1-(2,2-dimethyl-1-oxybutoxy)butyl]-4,6-dimethylphenyl]-3,5-dihydroxy-6-heptenoic acid methyl ester as an oil: IR (CHCl$_3$) 3480, 1715 and 1610 cm$^{-1}$; NMR (CDCl$_3$) δ 0.72–0.84 (3H, m), 0.91 (3H, t, J=9 Hz), 1.10–1.20 (6H, m), 1.20–2.00 (8H, m), 1.24 (3H, s), 2.30 (3H, s), 2.40–3.00 (2H, exchangeable), 2.50–2.60 (2H, m), 3.74 (3H, s), 4.34–4.52 (1H, m), 4.60–4.72 (1H, m), 5.66–5.84 (1H, m), 5.96–6.08 (1H, m), 6.64–6.74 (1H, m), 6.96 (1H, s), 7.05 (1H, s).

A solution of the ester prepared in the preceding paragraph (56.3 mg, 0.126 mmol) and 1N NaOH (126 μl, 0.126 mmol) in 4 mL of 95% EtOH were stirred at room temperature for 30 minutes. The reaction was partitioned between diethyl ether and 1N HCl and extracted. The aqueous layer was extracted with diethyl ether (two times) and the organic extracts combined, dried over $MgSO_4$ and the solvent removed under reduced pressure to give an oil (52 mg). A thin layer chromatogram indicated that lactonization had already occurred. Purification of the oil by column chromatography on silica gel (Merck, 230–400 mesh) using 1:1 hexane:ethyl acetate as an eluent gave the title compound as an oil (18 mg, 35%): IR (CHCl$_3$) 3400, 1715 and 1610 cm$^{-1}$; NMR (CDCl$_3$)δ 0.72–0.84 (3H, m), 0.90 (3H, t, J=8 Hz), 1.10–1.20 (6H, m), 1–20–2.20 (8H, m), 2.24 (CH$_3$, one diastereomer), 2.26 (CH$_3$, one diastereomer), 2.30 (3H, s), 2.64–2.76 (1H, m), 2.78–2.90 (1H, m), 4.44–4.54 (1H, m), 5.40–5.48 (1H, m), 5.74–5.90 (1H, m), 5.90–6.00 (1H, m), 6.74–6.86 (1H, m), 6.96 (1H, s), 7.05 (1H, s).

Elemental Analysis for: $C_{25}H_{36}O_5$ Calculated: C, 72.08; H, 8.71. Found: C, 71.40; H, 8.86.

The pyran-2-one is saponified with a suitable base such as sodium hydroxide to afford the pharmaceutically acceptable salt. Acidification yields the free carboxylic acid (3R, 5S, E)-7-[2-[1-(2,2-dimethyl-1-oxybutoxy)butyl]-4,6-dimethylphenyl]-3,5-dihydroxy-6-heptenoic acid.

EXAMPLE 2

2,2-Dimethylbutanoic acid[4α,6β(E)]-1-[2-[2-(tetrahydro-4-hydroxy-6-oxo-2H-pyran-2-yl)ethenyl]-3,5-dimethylphenyl]decyl ester In the manner described in Example 1, (E)-2-[2-(2-bromo-4,6-dimethylphenyl)ethenyl]-5,5-dimethyl-1,3-dioxane was reacted with n-decanal to obtain (E)-2-[2-(5,5-dimethyl-1,3-dioxan-2-yl)ethenyl]3,5-dimethyl-α-nonylbenzenemethanol as a white solid (955.4 mg, 38%): 59°–61° C.; IR (KBr) 3320, 2900, 2820, 1460 and 1375 cm$^{-1}$; NMR (DMSO-d$_6$) δ 0.72 (3H, s), 0.86 (3H, t, J=8 Hz), 1.14 (3H, s), 1.22 (14H, broad singlet), 1.40–1.56 (2H, m), 2.18 (3H, s), 2.26 (3H, s), 3.54 (2H, d, J=12 Hz), 3.64 (2H, d, J=12 Hz), 4.66–4.76 (1H, m), 4.90 (1H, d, J=5 Hz, exchangeable), 5.06 (1H, d, J=6 Hz), 5.58 (1H, dd, J=5, 15 Hz), 6.72 (1H, d, J=15 Hz), 6.92 (1H, s), 7.18 (1H, s).

Elemental Analysis for: $C_{26}H_{42}O_3$ Calculated: C, 77.56; H, 10.52. Found: C, 77.54; H, 10.68.

2,2-Dimethylbutyryl chloride (1.2 mL, 8.66 mmol) and 4-dimethylaminopyridine (1.17 g, 9.58 mmol) were added under a nitrogen atmosphere at room temperature to a solution of the alcohol prepared in the preceding paragraph (880 mg, 2.18 mmol) in 50 mL of methylene chloride. After the addition, the solution was stirred at room temperature for 5 hours. The solution was washed with 10% HCl, 10% NaHCO$_3$, dried (anh. K$_2$CO$_3$) and the solvent removed under reduced pressure. Purification of the residual oil on silica gel (230–400 mesh) using 4:1 methylene chloride:hexane as an eluent gave 2,2-dimethylbutanoic acid (E)-1-[2-[2-(5,5-dimethyl-1,3-dioxan-2-yl)-ethenyl]-3,5-dimethylphenyl]decyl ester as an oil (960 mg, 88%): IR (film) 2910, 2840 and 1720 cm$^{-1}$; NMR (DMSO-d$_6$) δ 0.66–0.78 (6H, m), 0.86 (3H, t, J=9 Hz), 1.02–1.20 (9H, m), 1.20–1.40 (14H, m), 1.50–1.70 (2H, m), 2.20 (3H, s), 2.24 (3H, s), 3.56 (2H, d, J=10 Hz), 3.64 (2H, d, J=10 Hz), 5.10 (1H, d, J=4 Hz), 5.68 (1H, dd, J=4, 15 Hz), 5.74–5.84 (1H, m), 6.78 (1H, d, J=15 Hz), 6.98 (2H, s).

As in Example 1, the 2,2-dimethylbutanoic acid (E)-1-[2-[2-(5,5-dimethyl-1,3-dioxan-2-yl)ethenyl]-3,5-dimethylphenyl]decyl ester was converted to 2,2-dimethylbutanoic acid (E)-1-[2-(formylethenyl)-3,5-dimethylphenyl]decyl ester which was produced as an oil (614 mg, 85%); IR (film) 2970, 2930, 2860, 1730 and 1695 cm$^{-1}$: NMR (CDCl$_3$) δ 0.78 (3H, t, J=8 Hz), 0.88 (3H, t, J=6 Hz), 1.16 (3H, s), 1.18–1.50 (14H, m), 1.54–1.76 (3H, m), 1.76–1.98 (1H, m), 2.34 (3H, s), 2.35 (3H, s), 5.74–5.86 (1H, m), 6.38 (1H, dd, J=8, 15 Hz), 7.02 (1H, s), 7.10 (1H, s), 7.92 (1H, d, J=15 Hz), 9.79 (1H, d, J=8 Hz).

The aldehyde was reacted with the dianion of acetoacetic acid methyl ester to afford (E)-7-[2-[1-(2,2-dimethyl-1-oxobutoxy)decyl]-4,6-dimethylphenyl]-5-hydroxy-2-oxo-6-heptenoic acid methyl ester as an oil (520 mg, 72%): IR (film) 3480, 2920, 2850, 2745 (sh) and 1715 cm$^{-1}$; NMR (CDCl$_3$) δ 0.72–0.82 (3H, m), 0.88 (3H, t, J=9 Hz), 1.10–1.20 (6H, m), 1.20–1.50 (14H, m), 1.54–1.74 (3H, m), 1.74–1.90 (1H, m), 2.22 (3H, s), 2.30 (3H, s), 2.88–2.96 (2H, m), 3.58 (2H, s), 3.78 (3H, s), 4.78–4.88 (1H, m), 5.64–5.80 (1H, m), 5.90–6.00 (1H, m), 6.66–6.76 (1H, m), 6.95 (1H, s), 7.04 (1H, s).

The 5-hydroxy-2-oxo-6-heptenoic acid ester was converted by borohydride reduction to (3R,5S,E)-7-[2-[1-(2,2-dimethyl-1-oxobutoxy)decyl]-4,6-dimethylphenyl]-3,5-dihydroxy-6-heptenoic acid methyl ester which was obtained as an oil (202 mg, 42%): IR (film) 3460, 2920, 2850 and 1725 cm$^{-1}$; NMR (CDCl$_3$) δ 0.72–0.82 (3H, m), 0.88 (3H, t, J=6 Hz), 1.10–1.20 (6H, m), 1.20–1.48 (14H, m), 1.52–1.90 (6H, m), 2.22 (3H, s), 2.29 (3H, s), 2.59 (2H, d, J=5 Hz), 2.60–3.00 (2H, m, exchangeable), 3.74 (3H, s), 4.32–4.44 (1H, m), 4.58–4.68 (1H, m), 5.64–5.78 (1H, m), 5.92–6.04 (1H, m), 6.62–6.72 (1H, m), 6.95 (1H, s), 7.03 (1H, s).

A solution of the dihydroxy ester obtained in the preceding paragraph (178 mg, 0.34 mmol) and 1N NaOH (335 μl, 0.34 mmol) in 10 mL of 95% EtOH was stirred at ice bath temperature for 30 minutes. The reaction was partitioned between 1N HCl and ethyl acetate and extracted. The organic layer was washed with water (two times), dried over MgSO$_4$ and the solvent removed under reduced pressure to give 163 mg of an oil. The oil was dissolved in 15 mL of dry toluene and the solution refluxed in a Dean-Stark apparatus for 7 hours. The solvent was removed under reduced pressure and the residual oil chromatographed on silica gel (Merck, 230–400 mesh) using 3:2 hexane-ethyl acetate as an eluent. The title compound was isolated as an oil (114 mg) in 68% overall yield: IR (film) 3460, 2960, 2930, 2860, 1720 and 1610 cm$^{-1}$; NMR (CDCl$_3$) δ 0.72–0.84 (3H, m), 0.88 (3H, t, J=7 Hz), 1.10–1.18 (6H, m), 1.26 (14H, broad singlet), 1.54–1.72 (3H, m), 1.72–1.90 (1H, m), 1.94–2.20 (2H, m), 2.24 (CH$_3$, one diastereomer), 2.25 (CH$_3$, one diastereomer), 2.30 (3H, s), 2.64–2.76 (1H, m), 2.76–2.90 (1H, m), 4.44–4.54 (1H, m), 5.38–5.48 (1H, m), 5.72–5.98 (2H, m), 6.72–6.86 (1H, m), 6.96 (1H, s), 7.04 (1H, s).

The pyran-2-one is saponified with a suitable base such as sodium hydroxide to afford the pharmaceutically acceptable salt. Acidification yields the free carboxylic acid (3R, 5S, E)-7-[2-[1-(2,2-dimethyl-1-oxobutoxy)decyl]-4,6-dimethylphenyl]-3,5-dihydroxy-6-heptenoic acid.

EXAMPLE 3

2,2-Dimethylbutanoic acid[4α,6β,(E)]-[[3,5-dimethyl-[2-[2-tetrahydro-4-hydroxy-6-oxo-2H-pyran-2-yl]ethenyl]phenyl]phenylmethyl]ester In the manner described in Example 1, (E)-2-[2-(2-bromo-4,6-dimethylphenyl)ethenyl]-5,5-dimethyl-1,3-dioxane was reacted with benzaldehyde to obtain (E)-2-[2-(5,5-dimethyl-1,3-dioxan-2-yl)ethenyl]3,5-dimethyl-α-phenylbenzenemethanol as a clear foam (271 mg, 81%): IR (film) 3420, 2940, 2840, 1660 and 1605 cm$^{-1}$; NMR (DMSO-d$_6$) δ 0.72 (3H, s), 1.14 (3H, s), 2.20 (3H, s), 2.24 (3H, s), 3.56 (2H, d, J=12 Hz), 3.64 (2H, d, J=12 Hz), 5.08 (1H, d, J=5 Hz), 5.64 (1H, dd, J=5, 15 Hz), 5.74 (1H, d, J=3 Hz, exchangeable), 5.90 (1H, d, J=3 Hz), 6.76 (1H, d, J=15 Hz), 6.96 (1H, s), 7.14 (1H, s), 7.16–7.36 (5H, m).

2,2-Dimethylbutyryl chloride (1.49 mL, 10.8 mmol) in 5 mL of methylene chloride was added dropwise to a solution of (E)-2-[2-(5,5-dimethyl-1,3-dioxan-2-yl)ethenyl]3,5-dimethyl-α-phenylbenzenemethanol (1.89 g, 5.4 mmol) and 4-dimethylaminopyridine (1.44 g, 11.8 mmol) in 75 mL of methylene chloride at 0° C. under a nitrogen atmosphere. After the addition the cooling bath was removed and the stirring continued for 2 hours. The solution was washed with 10% HCl, 10% NaHCO$_3$, dried (anh. K$_2$CO$_3$) and the solvent removed under reduced pressure. Purification of the residual oil on silica gel (Merck, 230–400 mesh) using 4:1 methylene chloride:hexane as an eluent gave 2,2-dimethylbutanoic acid (E)-1-[2-[2-(5,5-dimethyl-1,3-dioxan-2-yl)-ethenyl]-3,5-dimethylphenyl]phenylmethyl ester as an oil (2.37 g, 98%): IR (film) 2950, 2840, 1720 and 1605 cm$^{-1}$; NMR (DMSO-d$_6$) δ 0.64–0.78 (6H, m), 1.08–1.20 (9H, m), 1.50–1.64 (2H, m), 2.20 (3H, s), 2.26 (3H, s), 3.54 (2H, d, J=10 Hz), 3.64 (2H, d, J=10 Hz), 5.06 (1H, d, J=5 Hz), 5.64 (1H, dd, J=5, 15 Hz), 6.73 (1H, d, J=15 Hz), 6.92 (1H, s), 7.03 (1H, s), 7.08 (1H, s), 7.26–7.44 (5H, m).

The 2,2-dimethylbutanoic acid (E)-1-[2-[2-(5,5-dimethyl-1,3-dioxan-2-yl)-ethenyl]-3,5-dimethylphenyl]phenylmethyl ester was then converted to 2,2-dimethylbutanoic acid (E)-1-[2-(formylethenyl)-3,5-dimethylphenyl]phenylmethyl ester which was produced as a white crystalline material (1.60 g, 88%): mp 53°–56° C.; IR (KBr) 2930, 1715, 1670 and 1600 cm$^{-1}$; NMR (CDCl$_3$) δ 0.76 (3H, t, J=9 Hz), 1.18 (3H, s), 1.20 (3H, s), 1.64 (2H, q, J=9 Hz), 2.32 (6H, s), 6.27 (1H, dd, J=9, 15 Hz), 6.98 (1H, s), 7.08 (1H, s), 7.19 (1H, s), 7.20–7.39 (5H, m), 7.79 (1H, d, J=15 Hz), 9.67 (1H, d, J=9 Hz).

Elemental Analysis for: $C_{24}H_{28}O_3$ Calculated: C, 79.09; H, 7.74. Found: C, 78.96; H, 7.69.

The aldehyde from the preceding paragraph was reacted with the dianion of acetoacetic acid methyl ester to afford (E)-7-[2-[1-(2,2-dimethyl-1-oxobutoxy)-phenylmethyl]-4,6-dimethylphenyl]-5-hydroxy-2-oxo-6-heptenoic acid methyl ester as an oil (1.53 g, 75%): IR (film) 3480, 2960 and 1715 $cm^{-1}$; NMR ($CDCl_3$) δ 0.76 (3H, t, J=9 Hz), 1.18 (6H, s), 1.62 (2H, q, J=9 Hz), 2.22 (3H, s), 2.30 (3H, s), 2.77 (2H, d, J=6 Hz), 3.54 (2H, s), 3.76 (3H, s), 4.68–479 (1H, m), 5.52–5.68 (1H, m), 6.59–6.70 (1H, m), 7.00 (1H, s), 7.02–7.12 (2H, m), 7.20–7.40 (5H, m).

The 5-hydroxy-2-oxo-6-heptenoic acid ester was converted by borohydride reduction to (3R, 5S, E)-7-[2-[1-(2,2-dimethyl-1-oxobutoxy)phenylmethyl]-4,6-dimethylphenyl]-3,5-dihydroxy-6-heptenoic acid methyl ester, produced as an oil (824 mg, 64%): IR (film) 3470, 2970, 1730 and 1610 $cm^{-1}$; NMR ($CDCl_3$) δ 0.76 (3H, t, J=6 Hz), 1.20 (6H, s), 1.56–1.84 (4H, m), 2.25 ($CH_3$, one diastereomer), 2.26 ($CH_3$, one diastereomer), 2.29 (3H, s), 2.46–2.60 (2H, m), 2.60–3.30 (2H, exchangeable), 3.75 (3H, s), 4.30–4.39 (1H, m), 4.50–4.60 (1H, m), 5.54–5.70 (1H, m), 6.59–6.72 (1H, m), 7.01 (1H, s), 7.04–7.18 (2H, m), 7.20–7.40 (5H, m).

A solution of the dihydroxy ester obtained in the preceding paragraph (300 mg, 0.62 mmol) and 1N NaOH (622 μl, 0.62 mmol) in 15 mL of 95% EtOH were stirred at ice bath temperature for 30 minutes. The reaction was partitioned between 1N HCl and ethyl acetate and extracted. The organic layer was washed with water (two times), dried over $MgSO_4$ and the solvent removed under reduced pressure to give 267 mg of an oil. On standing at room temperature the oil (dihydroxy acid) lactonized to the title compound (solid foam, 108 mg, 38%): IR ($CHCl_3$) 3450, 1730 and 1615 $cm^{-1}$; NMR ($CDCl_3$) δ 0.76 (3H, t, J=8 Hz), 1.20 (6H, s), 1.64 (2H, q, J=8 Hz), 1.74–2.14 (2H, m), 2.26 (3H, s), 2.31 (3H, s), 2.58–2.84 (2H, m), 4.32–4.46 (1H, m), 5.28–5.40 (1H, m), 5.56–5.74 (1H, m), 6.68–6.80 (1H, m), 6.96–7.18 (3H, m), 7.20–7.40 (5H, m).

Elemenal Analysis for: $C_{28}H_{34}O_5$ Calculated: C, 74.64; H, 7.61. Found: C, 74.15; H, 8.15.

The pyran-2-one is saponified with a suitable base such as sodium hydroxide to afford the pharmaceutically acceptable salt. Acidification yields the free carboxylic acid (3R, 5S, E)-7-[2-[1-(2,2-dimethyl-1-oxobutoxy)phenylmethyl]-4,6-dimethylphenyl-3,5-dihydroxy-6-heptenoic acid.

EXAMPLE 4

2,2-Dimethylbutanoic acid [4α,6β(E)]-[[2-[2-tetrahydro-4-hydroxy-6-oxo-2H-pyran-2-yl)ethenyl]-3,5-dimethylphenyl]methyl]ester A 1.3M solution of n-butyllithium in hexane (5.6 mL, 7.40 mmol) was added dropwise over 10 minutes to a solution of (E)-2-[2-(2-bromo-4,6-dimethylphenyl)ethenyl]-5,5-dimethyl-1,3-dioxane (prepared as in Example 1) (2.01 g, 6.17 mmol) in 100 mL of anhydrous THF at −78° C. under a nitrogen atmosphere. After the addition was complete, the resulting yellow solution was stirred at −78° C. for 30 minutes. N-Formylmorpholine (744 μl, 7.40 mmol; dried over 3 A mol. sieves) was added and the solution stirred at −78° C. for 15 minutes. The cooling bath was removed and the stirring continued for 3.5 hours. After cooling the reaction mixture to ice bath temperature, aqueous $NH_4Cl$ was added and the reaction stirred at ice bath temperature for 30 minutes. The reaction was partitioned between aqueous $NH_4Cl$-diethyl ether and extracted. The organic layer was washed three times with water and then the solvent removed under reduced pressure to give 2.74 g of a yellow oil. Purification by high pressure liquid chromatography gave (E)-2-[2-(5,5-dimethyl-1,3-dioxan-2-yl)ethenyl]-3,5-dimethylbenzaldehyde as a crystalline material (1.31 g, 78%): mp 73°–80° C.; IR (KBr) 2960, 2860, 2760, 1685 and 1610 $cm^{-1}$; NMR (DMSO-$d_6$) δ 0.72 (3H, s), 1.14 (3H, s), 2.28 (3H, s), 2.34 (3H, s), 3.56 (2H, d, J=12 Hz), 3.65 (2H, d, J=12 Hz), 5.15 (1H, d, J=6 Hz), 5.63 (1H, dd, J=6, 15 Hz), 7.04 (1H, d, J=15 Hz), 7.38 (1H, s), 7.51 (1H, s), 10.08 (1H, s).

As prepared in the preceding paragraph, a solution of (E)-2-[2-(5,5-dimethyl-1,3-dioxan-2-yl)ethenyl]-3,5-dimethylbenzaldehyde (1.44 g, 5.24 mmol) in 75 mL of 4:1 THF-MeOH (previously dried over mol. sieves) was put under a nitrogen atmosphere and cooled to ice bath temperature. Sodium borohydride (238 mg, 6.29 mmol) was added in portions over 5 minutes to the above solution and the resulting mixture was stirred at ice bath temperature for 45 minutes. The reaction was cautiously layered between 1N HCl-ethyl acetate and extracted. The organic layer was washed with water (three times) and then the solvent removed under reduced pressure to give 1.64 g of an oil. Purification on 250 g of silica gel (Merck, 230–400 mesh) using 4:1 hexane-ethyl acetate as an eluent gave (E)-2-[2-(5,5-dimethyl-1,3-dioxan-2-yl)ethenyl]-3,5-dimethylbenzene-methanol as a clear oil (1.21 g, 83%): IR (film) 3410, 2950, 2850, 1660 and 1605 $cm^{-1}$; NMR (DMSO-$d_6$) δ 0.71 (3H, s), 1.12 (3H, s), 2.20 (3H, s), 2.26 (3H, s), 3.53 (2H, d, J=12 Hz), 3.62 (2H, d, J=12 Hz), 4.42 (2H, d, J=6 Hz), 5.00–5.10 (2H, m, one is exchangeable), 5.74 (1H, dd, J=6, 15 Hz), 6.74 (1H, d, J=15 Hz), 6.94 (1H, s), 7.13 (1H, s).

In the same manner as described in Example 3, the alcohol of the preceding paragraph was condensed with 2,2-dimethyl butyrylchloride to afford 2,2-dimethylbutanoic acid (E)-[2-[2-(5,5-dimethyl-1,3-dioxan-2-yl)ethenyl]-3,5-dimethylphenyl]methyl ester as an oil (1.15 g, 86%): IR (film) 2950, 2870, 2845, 1725 and 1615 $cm^{-1}$; NMR (DMSO-$d_6$) δ 0.72 (3H, s), 0.76 (3H, t, J=9 Hz), 1.10 (6H, s), 1.12 (3H, s), 1.52 (2H, q, J=9 Hz), 2.24 (3H, s), 2.27 (3H, s), 3.54 (2H, d, J=10 Hz), 3.62 (2H, d, J=10 Hz), 5.00 (2H, s), 5.05 (1H, d, J=5 Hz), 5.72 (1H, dd, J=5, 15 Hz), 6.78 (1H, d, J=15 Hz), 7.07 (2H, s).

Elemental Analysis for: $C_{23}H_{34}O_4$ Calculated: C, 73.76; H, 9.15. Found: C, 73.48; H, 9.07.

The 2,2-dimethylbutanoic acid (E)-1,-[2-[2-(5,5-dimethyl-1,3-dioxan-2-yl]-ethenyl]-3,5-dimethylphenyl]methyl ester was then converted to 2,2-dimethylbutanoic acid (E)-1-[2-(formylethenyl)-3,5-dimethylphenyl]methyl ester, which was obtained as an oil (726 mg, 92%): IR (film) 2980, 2930, 2880, 1725, 1690, 1630 and 1610 $cm^{-1}$; NMR ($CDCl_3$) δ 0.80 (3H, t, J=6 Hz), 1.16 (6H, s), 1.57 (2H, q, J=6 Hz), 2.36 (3H, s), 2.39 (3H, s), 5.12 (2H, s), 6.44 (1H, dd, J=9, 15 Hz), 7.11 (1H, s), 7.16 (1H, s), 7.74 (1H, d, J=15 Hz), 9.76 (1H, d, J=9 Hz).

Elemental Analysis for: $C_{18}H_{24}O_3$ Calculated: C, 74.97; H, 8.39. Found: C, 74.22; H, 8.06.

The aldehyde was reacted with the dianion of acetoacetic acid methyl ester to afford (E)-7-[2-[1-(2,2- dimethyl-1-oxobutoxy)methyl]-4,6-dimethylphenyl]-5-hydroxy-2-oxo-6-heptenoic acid methyl ester as an oil (637 mg, 69%): IR (film) 3500, 2970, 2930 (SH), 2880, 1750 (sh), 1715, 1635 and 1610 cm$^{-1}$; NMR (CDCl$_3$) δ 0.83 (3H, t, J=8 Hz), 1.17 (6H, s), 1.58 (2H, q, J=8 Hz), 2.27 (3H, s), 2.32 (3H, s), 2.20–2.50 (1H, exchangeable), 2.90 (2H, d, J=6 Hz), 3.57 (2H, s), 3.77 (3H, s), 4.76–4.84 (1H, m), 5.05 (1H, d, J=13 Hz), 5.12 (1H, d, J=13 Hz), 5.73 (1H, dd, J=6, 15 Hz), 6.67 (1H, d, J=15 Hz), 7.02 (1H, s), 7.07 (1H, s).

The 5-hydroxy-2-oxo-6-heptenoic acid ester was converted by borohydride reduction to (3R,5S,E)-7-[2-[1-(2,2-dimethyl-1-oxobutoxy)methyl]-4,6-dimethylphenyl]-3,5-dihydroxy-6-heptenoic acid methyl ester as an oil (305 mg, 56%): IR (film) 3450, 2960, 2870, 1715, 1610 cm$^{-1}$; NMR (CDCl$_3$) δ 0.82 (3H, t, J=9 Hz), 1.16 (6H, s), 1.58 (2H, q, J=9 Hz), 1.66–1.90 (2H, m), 2.27 (3H, s), 2.32 (3H, s), 2.56 (2H, d, J=6 Hz), 2.66–3.10 (1H, exchangeable, 3.74 (3H, s), 4.30–4.44 (1H, m), 4.54–4.66 (1H, m), 5.06 (1H, d, J=13 Hz), 5.14 (1H, d, J=13 Hz), 5.73 (1H, dd, J=6, 15 Hz), 6.63 (1H, d, J=15 Hz), 7.02 (1H, s), 7.08 (1H, s).

Elemental Analysis for: C$_{23}$H$_{34}$O$_6$ Calculated: C, 67.96; H, 8.43. Found: C, 67.43; H, 8.44.

In the same manner as described in Example 2, the dihydroxy ester obtained in the preceding paragraph was converted to the title compound which was obtained as an oil (34 mg, 20%): IR (CHCl$_3$) 3410, 1715 and 1610 cm$^{-1}$; NMR (CDCl$_3$) δ 0.82 (3H, t, J=9 Hz), 1.16 (6H, s), 1.59 (2H, q, J=9 Hz), 1.90–2.08 (1H, m), 2.10–2.20 (1H, m), 2.26 (3H, s), 2.32 (3H, s), 2.10–2.60 (1H, exchangeable), 2.64–2.76 (1H, m), 2.76–2.88 (1H, m), 4.20–4.52 (1H, m), 4.04 (1H, d, J=14 Hz), 4.10 (1H, d, J=14 Hz), 5.34–5.46 (1H, m), 5.78 (1H, dd, J=6, 15 Hz), 6.74 (1H, d, J=15 Hz), 7.03 (1H, s), 7.08 (1H, s).

The pyran-2-one is saponified with a suitable base such as sodium hydroxide to afford the pharmaceutically acceptable salt. Acidification yields the free carboxylic acid (3R, 5S, E)-7-[2-[1-(2,2-dimethyl-1-oxybutoxy)methyl]-4,6-dimethylphenyl]-3,5-dihydroxy-6-heptenoic acid.

The HMG-CoA reductase inhibitory properties of representative compounds of this invention were established by subjecting the compounds to the following standard experimental test procedure adapted from Rodwell et al., Adv. Lipid Res. 14 1, 1976; Endo et al., FEBS Letters 72 323, 1976; and Tanzawa et al., Biochemia et Biophysica Acta 488 97, 1977.

Rat livers obtained from rats fed on a diet containing 3% cholestyramine and maintained on a reverse lighting regimen for three weeks are homogenized and the microsomal fraction is isolated by differential ultra centrifugation to obtain the HMG-CoA reductase enzyme. To a preincubated (five minutes at 37° C.) solution of the compound being tested (as either the lactone and/or dihydroxy sodium carboxylate in amounts from 10$^{-3}$ to 10$^{-6}$M) in TEDKS$_{100}$pH (Tris® 40 mM; EDTA 1 mM; dithiothreitol 5 mM; KCl 70 mM; sucrose 100 mM) 7.5 buffer or DMSO dissolved in an assay medium containing 20 μl of 2.5M KCl; 20 μl NADPH (reduced nicotinamide adenine dinucleotide phosphate) (7.5 mM); and 40 μl of labeled (RS) HMG-CoA (3-$^{14}$C; 0.4 Ci; 200 μM) is added 10 μl of preincubated (five minutes at 37° C.) microsomal fraction (produced above) to obtain a total volume of 125 μl. After a twenty minute incubation period at 37° C., reaction of the enzyme is terminated by addition of 10 μl of 70% of HClO$_4$. The assay tubes are then centrifuged for two minutes in a Beckman microfuge II.

To 100 μl of the supernatant liquid is added 10 μl of non-radioactive mevalonic acid lactone (0.25M in 8 mM H$_2$SO$_4$). An aliquot of the sample is eluted with 8 mM H$_2$SO$_4$ through Bio Rad Aminex HPX-87H (HPLC: Hewlett-Packard Model 1084B) at a flow rate of 1 mL/minute. The effluent is fractionated, Hydrofluor® is added and radioactivity of the [$^{14}$C] mevalonolactone produced by reduction of [$^{14}$C] HMG-CoA determined with a scintillation counter.

The percent inhibition of HMG-CoA reductase activity is obtained by comparison with a control assay devoid of the test compound. The inhibitory concentration (IC$_{50}$) is calculated for the various test compounds.

The results of these experiments were as follow:

| Inhibition of HMG-CoA Reductase (IC$_{50}$, M) | | |
|---|---|---|
| | Lactone | Dihydroxycarboxylate |
| Mevinolin (Standard) | 6 × 10$^{-7}$ | 5 × 10$^{-9}$ |
| Example 1 | 2.7 × 10$^{-6}$ | 1.7 × 10$^{-6}$ |
| Example 2 | >10$^{-3}$ | >10$^{-4}$ |
| Example 3 | 1.7 × 10$^{-3}$ | 6.2 × 10$^{-6}$ |
| Example 4 | 5.7 × 10$^{-5}$ | 4.0 × 10$^{-5}$ |

Thus, the compounds of this invention are established as potent inhibitors of HMG-CoA reductase, which categorizes them as anti-hypercholesteremic agents useful in the treatment of disease states in which reduced levels of cholesterol are desired, such as atherosclerosis, familial hypercholesterolaemia, hyperlipaemia, and the like.

Administration of the compounds of this invention, in suitable dosage form, may be by the oral or parenteral routes, in single or plural doses as neded to reduce cholesterol blood plasma levels. The specific dosage regimen for a given patient will depend upon age, size, pathological state, severity of dysfunction, etc. and may be individualized by the attending physician by following blood lipid levels. Sustained release formulations for oral administration by tablet or capsule are especially suitable for administration of the HMG-CoA reductase inhibitors of this invention.

What is claimed is:

1. A compound of the formula:

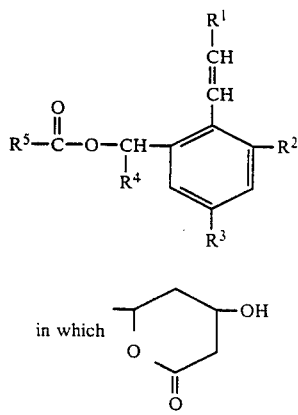

where

M is hydrogen or alkyl of 1 to 4 carbon atoms;

$R^2$ and $R^3$ are, independently, alkyl of 1 to 6 carbon atoms;

$R^4$ is hydrogen, alkyl of 1 to 10 carbon atoms, trifluoromethyl, phenyl or substituted phenyl, where the substituent is alkyl of 1 to 8 carbon atoms, alkoxy of 1 to 8 carbon atoms, or trifluoromethyl; and $R^5$ is alkyl of 1 to 10 carbon atoms, phenyl or substituted phenyl where the substituent is alkyl of 1 to 8 carbon atoms, alkoxy of 1 to 8 carbon atoms, or trifluoromethyl;

or a pharmaceutically acceptable salt thereof.

2. A compound of claim 1 of the formula:

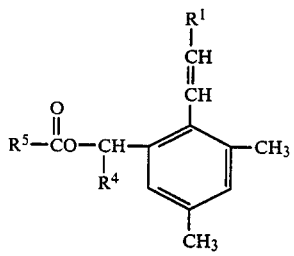

in which 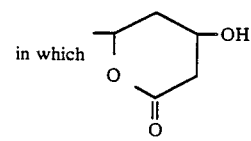

where
M is hydrogen or alkyl of 1 to 4 carbon atoms;
$R^4$ is hydrogen, alkyl of 1 to 10 carbon atoms or phenyl; and
$R^5$ is alkyl of 1 to 6 carbon atoms;
or a pharmaceutically acceptable salt thereof.

3. The compound of claim 1 which is 2,2-dimethylbutanoic acid [4α,6β-(E)]-1-[2-[2-tetrahydro-4-hydroxy-6-oxo-2H-pyran-2yl)ethenyl]-3,5-dimethylphenyl]-butyl ester.

4. The compound of claim 1 which is 2,2-dimethylbutanoic acid [4α,6β-(E)]-1-[2-[2-(tetrahydro-4-hydroxy-6-oxo-2H-pyran-2-yl)ethenyl]-3,5-dimethylphenyl]-decyl ester.

5. The compound of claim 1 which is 2,2-dimethylbutanoic acid [4α,6β,-(E)]-[[3,5-dimethyl-[2-[2-tetrahydro-4-hydroxy-6-oxo-2H-pyran-2-yl]ethenyl]phenyl]-phenylmethyl]ester.

6. The compound of claim 1 which is 2,2-dimethylbutanoic acid [4α,6β-(E)]-[[2-[2-tetrahydro-4-hydroxy-6-oxo-2H-pyran-2-yl)ethenyl]-3,5-dimethylphenyl]-methyl]ester.

* * * * *